(12) United States Patent
Thompson

(10) Patent No.: US 10,213,351 B2
(45) Date of Patent: Feb. 26, 2019

(54) MOBILE SCREENING APPARATUS

(71) Applicant: FRAZER, LTD., Houston, TX (US)

(72) Inventor: Barry Thompson, Houston, TX (US)

(73) Assignee: FRAZER, LTD., Houston, TX (US)

( * ) Notice: Subject to any disclaimer, the term of this patent is extended or adjusted under 35 U.S.C. 154(b) by 159 days.

(21) Appl. No.: 15/433,109

(22) Filed: Feb. 15, 2017

(65) Prior Publication Data

US 2017/0231843 A1 Aug. 17, 2017

Related U.S. Application Data

(60) Provisional application No. 62/295,222, filed on Feb. 15, 2016.

(51) Int. Cl.
| | | |
|---|---|---|
| *A61B 6/00* | (2006.01) | |
| *A61G 3/00* | (2006.01) | |
| *A61B 6/03* | (2006.01) | |
| *A61B 6/04* | (2006.01) | |
| *A61G 3/06* | (2006.01) | |

(52) U.S. Cl.
CPC ............ *A61G 3/001* (2013.01); *A61B 6/032* (2013.01); *A61B 6/0407* (2013.01); *A61B 6/4405* (2013.01); *A61B 6/50* (2013.01); *A61B 6/56* (2013.01); *A61G 3/062* (2013.01)

(58) Field of Classification Search
CPC .......... A61G 3/001; A61G 3/062; A61B 6/50; A61B 6/56; A61B 6/4405; A61B 6/032; A61B 6/0407
USPC ...................................................... 296/24.38
See application file for complete search history.

(56) References Cited

U.S. PATENT DOCUMENTS

| | | | | |
|---|---|---|---|---|
| 4,181,347 A | * | 1/1980 | Clark ................... | A61B 6/4405 280/763.1 |
| 4,449,746 A | * | 5/1984 | Clark ................... | A61B 6/4488 280/763.1 |
| 5,097,497 A | * | 3/1992 | Deucher .............. | A61B 6/4405 378/196 |
| 5,755,478 A | | 5/1998 | Kamiya et al. | |
| 6,038,469 A | * | 3/2000 | Karlsson .............. | A61B 5/0006 600/509 |
| 6,082,799 A | * | 7/2000 | Marek ...................... | B60P 3/14 296/19 |
| 6,481,887 B1 | * | 11/2002 | Mirabella ............ | A61B 6/4405 296/24.38 |
| 6,625,252 B2 | | 9/2003 | Mirabella | |
| 7,347,472 B2 | * | 3/2008 | Pellegrin, Jr. .......... | A61G 3/001 296/24.38 |

(Continued)

*Primary Examiner* — Pinel E Romain
(74) *Attorney, Agent, or Firm* — Egbert Law Offices, PLLC

(57) ABSTRACT

A mobile screening apparatus has a patient compartment having a floor, and end wall, a first sidewall and a second sidewall. The second sidewall has an expanding wall that is movable between a retracted position and an extended position. The mobile screening apparatus also has a scanner positioned in the patient compartment. The scanner has a length dimension extending longitudinally within the patient compartment. A scanning table is positioned within the patient compartment. The scanning table is movable in relation to the scanner. The patient compartment is positioned upon a chassis of a vehicle. A generator is connected to the scanner so as to supply power to the scanner. In particular, the scanner is a lung scanner.

18 Claims, 8 Drawing Sheets

(56) References Cited

U.S. PATENT DOCUMENTS

| | | |
|---|---|---|
| 7,794,001 B2 | 9/2010 | Blackwell et al. |
| 8,459,714 B2 | 6/2013 | Pomper et al. |
| 8,888,495 B2 * | 11/2014 | Johnson .................. G09B 5/06 434/219 |
| 9,308,141 B2 * | 4/2016 | Blackwell .............. A61G 3/001 |
| 2014/0155740 A1 | 6/2014 | Semenov |
| 2015/0282774 A1 * | 10/2015 | Lee ........................ A61B 6/032 378/8 |

* cited by examiner

MOBILE SCREENING APPARATUS

CROSS-REFERENCE TO RELATED APPLICATIONS

The present application claims priority from the U.S. Provisional Patent Application Ser. No. 62/295,222, filed on Feb. 15, 2016, and entitled "Mobile Screening Clinic".

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to vehicles that have body screening devices therein. More particularly, the present invention relates to mobile clinics that allow for the scanning of the body of a patient. More particularly, the present invention relates to mobile lung screening systems.

2. Description of Related Art Including Information Disclosed Under 37 CFR 1.97 and 37 CFR 1.98.

Lung screening is an important diagnostic tool for evaluating the condition of lungs of a patient. Unfortunately, virtually all lung screening must be carried out in a hospital or clinical environment. As such, for a patient to obtain the requisite lung screening, the patient must travel to the hospital and/or clinic so as to have the diagnostic procedures carried out at that time. Typically, lung screening will determine the condition of a patient's lungs, whether there are potential signs of cancer, and whether there any traumatic events that have adversely affected the lungs of the patient.

Whenever patients are required to travel to a hospital or clinic environment in order to have lung screening carried out, then the patient may be discouraged from having these important diagnostic procedures carried out. A need has developed so as to provide lung screening in remote locations so that patients can easily access the required care.

Unfortunately, conventional body screening devices are very complex, require great deal of equipment and controls, and generally are not compatible with mobile application. However, in recent years, there have been new products BODYTOM (™) and a CERETOM (™) manufactured and sold by Samsung. These products are transportable screening systems.

The BODYTOM (™) is a multi-departmental imaging solution capable of transforming any room in the hospital into an advanced imaging suite. It is a portable, full-body, 32-slice computed tomography scanner. The system has an 85 centimeter gantry and a 60 centimeter field of view. This BODYTOM (™) is battery-powered and has an internal drive system that can be easily transported from room-to-room. The BODYTOM (™) is compatible with PACS, EMR, planning systems, surgical and robotic navigation systems. The BODYTOM (™) is uniquely designed to accommodate patients of all sizes. It provides a point-of-care CT imaging wherever high-quality CT images are needed. The combination of rapid scan time, flexible settings, and immediate image viewing makes the BODYTOM (™) a valuable tool to any facility requiring versatile real-time portable imaging.

The CERETOM (™) is an eight 8-slice small-bore portable CT scanner that delivers high-quality non-contrast, and angiography, and contrast perfusion and scans in a variety of patient locations. It also has rapid scan time, easy-to-use interface, and immediate image viewing.

Unfortunately, the size of these devices makes them impractical for use in an ambulance. Typically, the interior of the patient compartment of an ambulance is not large enough or wide enough to accommodate such equipment. As such, it is been felt that such devices would not be suitable for use in a mobile clinic environment. Additionally, since the lengthwise dimension of the BODYTOM (™) exceeds the width requirements for loads on roadways, it was felt that this piece of equipment would not be compatible with mobile applications.

In the past, various patents and patent publications have issued with respect to mobile clinics and mobile scanning devices. In particular, U.S. Pat. No. 5,755,478, issued on May 26, 1998 to Kamiya et al., describes a mobile self-contained trauma care system. This trauma care system includes a vehicle body having a floor, sidewalls, and wheels. There are a plurality of patient supports affixed to the sidewalls of the vehicle body. A central treatment module receives various treatment modules that are removably positioned on the floor. A treatment table is affixed to the floor and generally is centered above the treatment module.

U.S. Pat. No. 6,625,252, issued on Sep. 23, 2003 to T. J. Mirabella, describes an emergency vehicle with a medical imaging scanner and teleradiology. The system is incorporated into an ambulance or other vehicle so as to permit a patient be diagnosed while enroute to a treatment facility, such as a trauma center. The system obtains medical image data while the patient is being transported in the vehicle and transports the medical image data to a receiver at a location which is remote from the vehicle. At the remote location, the transmitted medical image data is displayed in a humanly discernible manner and interpreted by a qualified physician, who then communicates diagnostic information to the technicians in the vehicle and/or to the testing physicians at the treatment facility. By providing diagnostic information back to the treating physicians prior to the patient's arrival at the treatment facility, the patient can be routed directly to the operating room, or the intensive care unit, as necessary, thereby saving valuable time.

U.S. Pat. No. 7,794,001, issued on Sep. 14, 2010 to Blackwell et al., provides a mobile medical facility that is capable of treating a plurality of patients and is transportable over roadways. In general, the mobile medical facility includes a trailer. The trailer defines a floor area and has at least a first and second configuration. In the first configuration, the floor area is reduced to allow for transporting of the trailer over the public highways. In the second configuration, the floor area of the trailer is expanded and large enough to support a plurality of beds for treating patients.

U.S. Pat. No. 8,459,714, issued on Jun. 11, 2013 to Pomper et al., describes a mobile radiation therapy system so as to provide appropriate treatment at a patient's home residence. A mobile x-ray team can be dispatched to the patient's home. A technical team reviews patient data to determine a proper therapy plan. The mobile radiation therapy apparatus is dispatched to the patient's home as required by the therapy plan. The mobile radiation therapy apparatus includes a radiation source and shielding. It is capable of superficial radiation therapy and/or high dose rate, low dose rate, and medium dose rate implant therapy and/or particle therapy.

U.S. Patent Application Publication No. 2014/0155740, published on Jun. 5, 2014 to S. Y. Semenov, describes an electromagnetic tomography system for gathering measurement data pertaining to a human head and includes an image chamber unit, a control system, and a housing. The image chamber unit includes an antenna assembly defining a horizontally-oriented imaging chamber and including an array of antennas arranged around the imaging chamber. The antennas include at least some transmitting antennas and some receiving antennas. The control system causes the transmitting antennas to transmit a low-power electromagnetic field that is received by the receiving antennas after passing through a patient's head in the imaging chamber.

It is an object of the present invention to provide a mobile scanning clinic that provides effective lung screening.

It is another object of the present invention to provide a screening clinic in which the screening can be carried out in remote locations.

It is another object of the present invention provide a mobile screening clinic that is compatible with Department of Transportation (DOT) standards.

It is another object of the present invention provide a mobile screening clinic that maintains a proper orientation of the screening vehicle.

It is still another object of the present invention provide a mobile screening clinic that allows a full crew to travel with the scanning system.

It is still a further object of the present invention to provide a mobile screening clinic that can be used in areas that lack external power supplies.

It is still another object of the present invention to provide a mobile screening clinic that enhances the maneuverability the screening vehicle.

These and other objects and advantages of the present invention will become apparent from a reading of the attached specification and appended claims.

BRIEF SUMMARY OF THE INVENTION

The present invention is a mobile screening apparatus that comprises a patient compartment and a scanner. The patient compartment has a floor, an end wall, a first sidewall and a second sidewall. The second sidewall has an expanding wall that is movable between a retracted position and an extended position. The scanner is positioned in the patient compartment. The scanner has a length dimension and a width dimension. The length dimension extends longitudinally within the patient compartment. The length dimension is greater than the width dimension. The scanner has a circular or oval opening.

A scanning table can be positioned in the patient compartment. The scanning table is movable in relation to the scanner. The scanning table has a surface thereon adapted to allow a body to be positioned thereon.

The mobile screening apparatus further includes a vehicle having a chassis upon which the patient compartment is positioned. The vehicle has wheels rotatably mounted to the chassis so as to allow the vehicle to move along an underlying surface. The vehicle has a cabin position forwardly of the patient compartment. A generator is connected to the scanner so as to supply power to the scanner. The generator can be mounted to the patient compartment or to the vehicle. A leveling mechanism is connected to either the patient compartment or to the chassis of the vehicle. The leveling mechanism is adapted to adjust the floor of the patient compartment to a horizontal orientation relative to an underlying surface. The leveling mechanism includes at least a first leveling leg and a second leveling leg. The first and second leveling legs extends downwardly from the floor. The first leveling leg is in spaced relation to the second leveling leg.

The retracted position of the expanding wall is generally flush with the second sidewall. The first sidewall is a fixed wall.

The scanner is movable within the patient compartment between a first position adjacent to the first sidewall and a second position generally centrally of the patient compartment. The scanner is at the first position when the expanding wall is in the extended position. The scanner is in the second position when the expanding wall is in the retracted position. In particular, a tracking plate is affixed to the floor of the patient compartment. A slide plate is received by the tracking plate. The slide plate is movable from one end to the opposite end of the tracking plate as the scanner moves between the first and second positions. A locking pin is received by the tracking plate and the slide plate so as to fix the position of the scanner in the patient compartment.

The scanning table is movable between a stowed position and an active position. The stowed position is against the expanding wall when the expanding wall is in the retracted position. The scanning table extends transverse to the expanding wall when expanding wall is in the extended position.

In the present invention, the scanner is a lung scanner. A control system is positioned in the patient compartment and cooperative with the scanner. The floor of the patient compartment has an area when the expanding wall is in the extended position that is greater than an area when the expanding wall is in the retracted position. The patient compartment has a first door on one of the sidewalls. The patient compartment has a second door at the end wall.

A control system is cooperative with the scanner so as to control the operation of the scanner and also to obtain diagnostic results from the scanner. A wheelchair lift is positioned adjacent to the second door at the end wall of the patient compartment so as to facilitate the ability to introduce wheelchairs into the patient compartment. A privacy curtain can extend within the patient compartment. As such, a patient is able to change clothes or to undress in privacy within the patient compartment.

In normal use, the vehicle can be driven to a desired location. A patient will enter through the first door at the sidewall of the patient compartment and enter the interior of the patient compartment. The patient will undress, as required, behind the privacy curtain. The patient can then lie on the scanning table in a proper position for scanning. The scanning table can move from the stowed position to the active position so that the body of the patient can be scanned by the scanner. A technician at the control system can then carry out the proper scanning and receive the results. Other technicians and physicians, as required, can also be able to observe the information provided from the scanning system at the control area. Various other displays can be incorporated within the patient compartment so as to allow for proper diagnoses to be carried out.

Following scanning, the patient can be moved from the scanning table and out of the patient compartment. The scanning table can be moved back to its stowed position. The expanding wall is retracted and the scanner is moved to the second position so that the mobile screening clinic moved to another location.

This foregoing Section is intended to describe, with particularity, the preferred embodiments of the present invention. It is understood that modifications to these preferred embodiments can be made within the scope of the appended claims. As such, this Section should not be construed, and anyway, as limiting the broad scope of the present invention. The present invention should only be limited by the following claims and their legal equivalents.

DETAILED DESCRIPTION OF THE INVENTION

Figure 1:
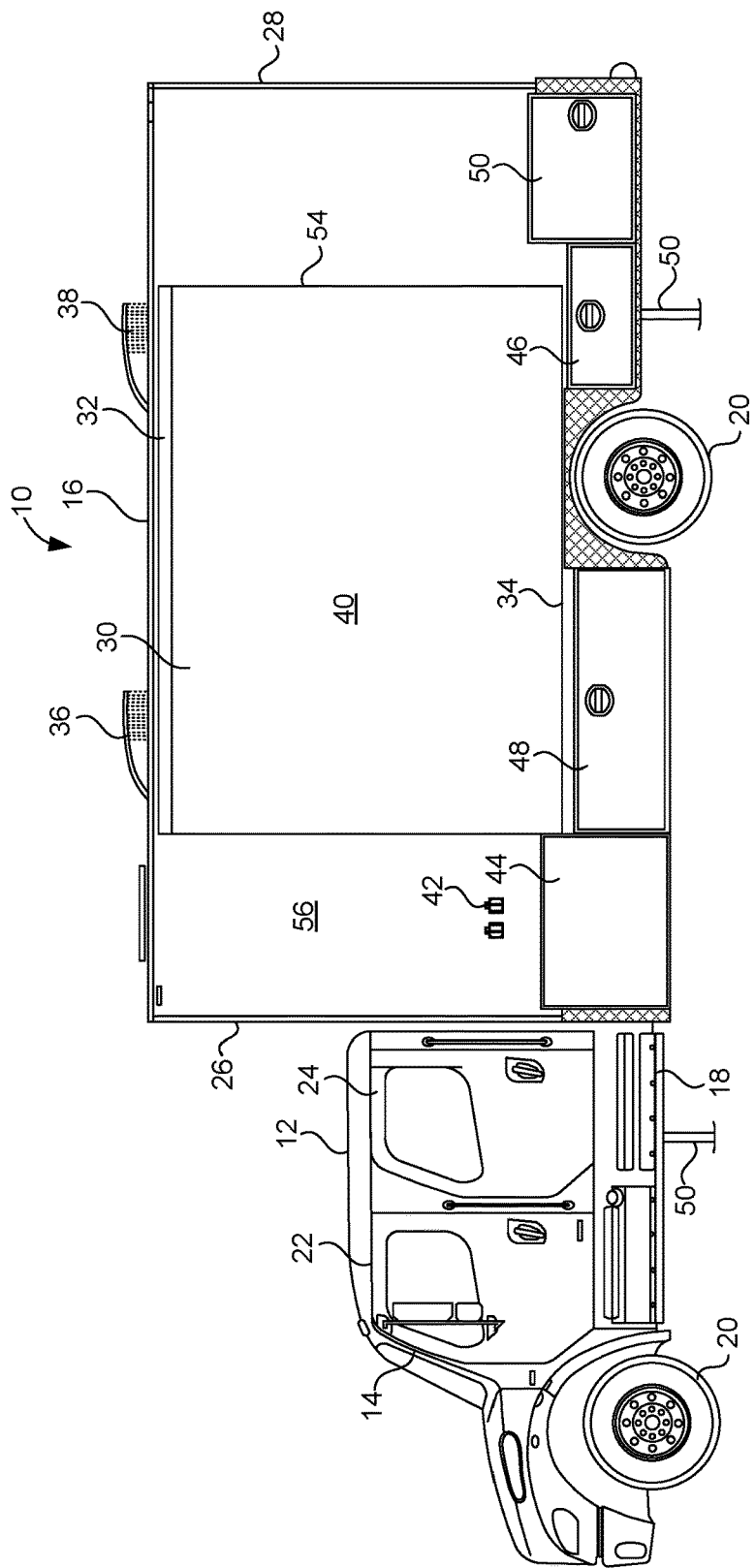
FIG. 1 is a side elevational view of the mobile screening apparatus in accordance with the teachings of the present invention.

Referring to FIG. 1, there is shown the mobile screening apparatus 10 in accordance with the preferred embodiment of the present invention. The mobile screening apparatus 10 includes a vehicle 12 having a cabin 14, a patient compartment 16, a chassis 18 and wheels 20. The wheels 20 are adapted to allow the mobile screening apparatus 10 to move on an underlying surface, such as a road. The chassis 18 is supported by the wheels 20 above the underlying surface. The cabin 14 is mounted on the chassis 18 and supported by the forward wheels 20. The cabin 14 includes a pair of doors 22 and 24 on each side of the cabin 14. As such, two rows of seats are provided on the interior of the cabin 12. This will accommodate an entire team of technicians. As such, the entire team of technicians can travel with the mobile screening apparatus 10. The use of the two rows of seats within the cabin 14 also avoids the need to have any personnel travel in the patient compartment 16.

The patient compartment 16 is positioned on the chassis 18 behind the cabin 14. The patient compartment 16 has a box-type structure with a forward wall 26, and end wall 28 a sidewall 30, a ceiling 32 and a floor 34. A pair of air-conditioning units 36 and 38 are provided on the ceiling 32. These walls will define the interior 40 of the patient compartment 16. The patient compartment 16 can also include 50 amp and 30 amp shore power connections 42, an exterior storage compartment 48, a generator compartment 44, and additional storage compartments 46 and 50. The generator compartment 44 can include an Onan generator that is capable of producing seven kilowatts of power. The other storage compartments 46 and 50 allow access to the hydraulic pump, the wheelchair controls, the generator, and the acknowledgment switches. These compartments 44, 46, 48 and 50 are generally positioned at the sidewall 30 of the patient compartment 16 and below the floor 30.

Importantly, the patient compartment 16 or the chassis 18 includes a leveling system 50. The leveling system 50 includes a pair of leveling legs that extend outwardly from the chassis 18 below the patient compartment 16. As such, when the wheels 20 are on an uneven or non-horizontal contour, the leveling legs 50 can be lowered so as to cause the floor 34 of the patient compartment 16 to have a proper horizontal orientation.

Importantly, the sidewall 30 includes an expanding wall 54. The expanding wall 54 is illustrated in its retracted position generally flush with the remainder 56 of the side wall 30. The expanding wall 54 is in the nature of a bump-out wall that is conventionally used in recreational vehicles. The expanding wall 54 will allow the interior volume 40 of the patient compartment 16 to expand and will allow the footprint of the floor 34 to expand.

Figure 2:
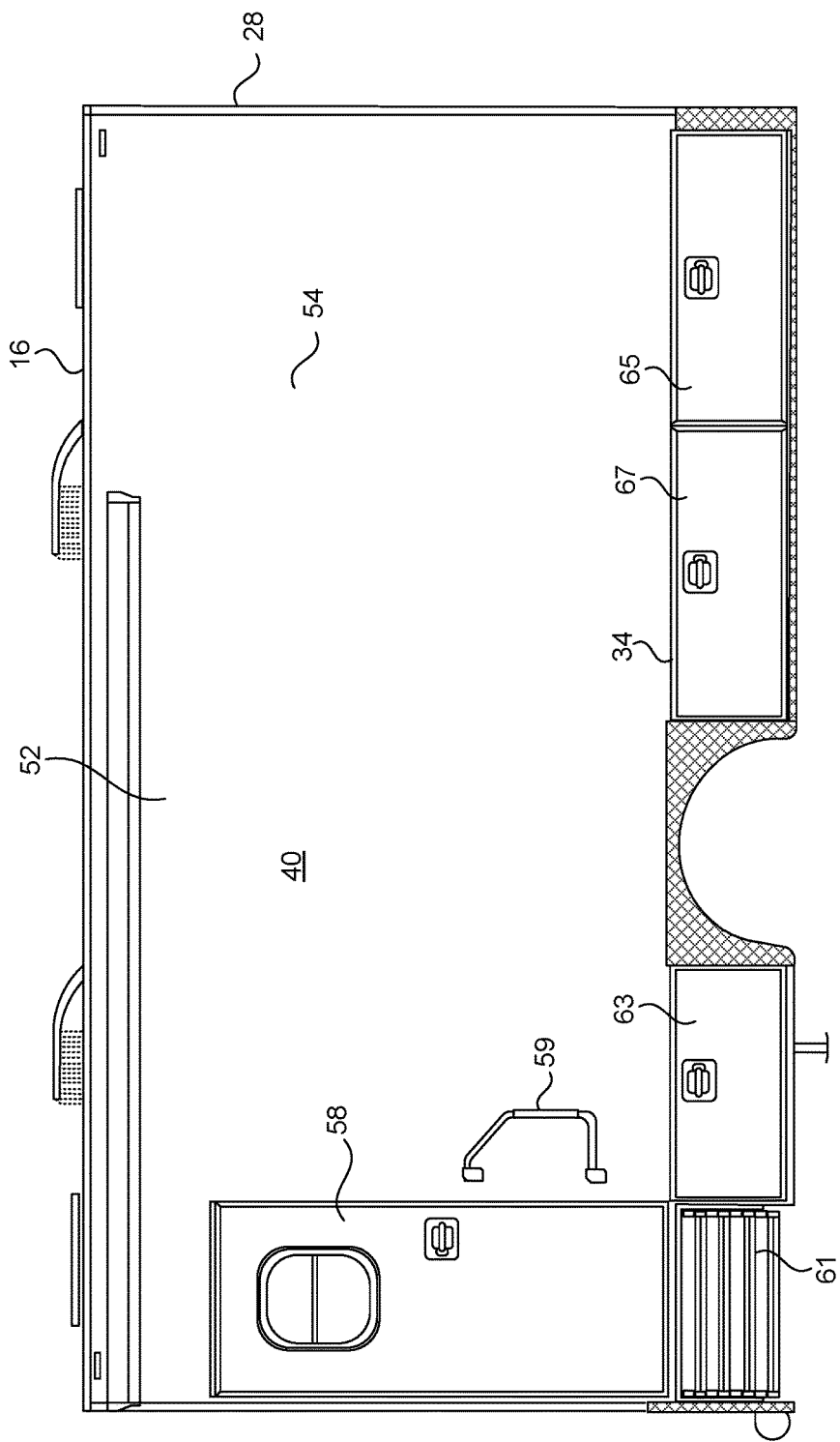
FIG. 2 is an opposite side view of the patient compartment of the mobile screening apparatus of the present invention.

FIG. 2 shows the opposite side of the patient compartment 16. This opposite sidewall 52 includes a first door 58 that can open to the interior 40 of the patient compartment 16. The first door 58 is located generally adjacent to the cabin 14 of the vehicle 12. A foldout-out handle 59 is located adjacent to the door 54. The handle 59 can be moved from a position generally adjacent to the sidewall 52 to a position transverse thereto so as to facilitate griping by patients and/or technicians entering the interior 40 of the patient compartment 16 through the door 58. Steps 61 are located below the floor 34 of the patient compartment 16. Steps 61 can be folded outwardly so as to allow patients and technicians to easily enter through the door 58. Exterior storage compartments 63 and 65 are provided below the floor 34. An electrical compartment 67 is also located below the floor 34.

Figure 3:
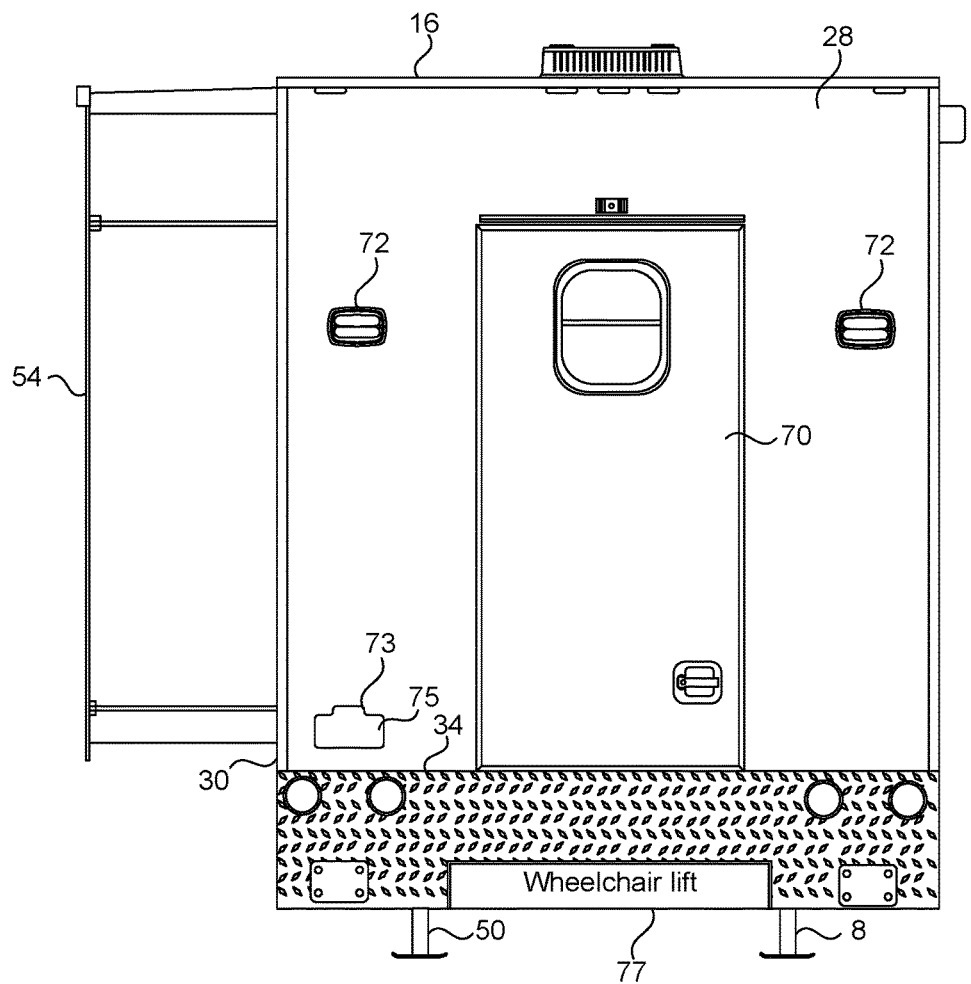
FIG. 3 is a rear view of the mobile screening apparatus of the present invention.

FIG. 3 shows the rear wall 28 of the patient compartment 16. The rear wall 28 has a second door 70 thereon. The second door 70 can open outwardly so as to provide a large entranceway into the interior 40 of the patient compartment 16. Various taillights 72 are provided at the rear wall 28. An LED illuminator 73 is provided for license plate 75. A wheelchair lift 77 is located below the second door 70. Wheelchair lift 77 can be extended outwardly so as to allow a wheelchair to be placed thereon. Wheelchair lift 77 can then moved upwardly so as to be located adjacent to the bottom of the door 70 so as to allow a wheelchair patient enter the interior 40 of the patient compartment 16. The leveling legs 50 are illustrated as extending downwardly generally adjacent to the end wall 28 of the patient compartment 16. It can be seen that the leveling legs 50 are in spaced relation to each other.

In FIG. 3, it can be seen that the expanding wall 54 is in its extended orientation. The expanding wall 54 extends outwardly from the sidewall 30 of the patient compartment 16. The expanding wall 54 extends outwardly from the sidewall 30 for a considerable distance. It can also be seen that the expanding wall 54 also extends the area of the floor 34 of the patient compartment.

The leveling legs 50 are hydraulically-operated so as to expand upwardly or downwardly. Each of the leveling legs 50 includes a foot at the bottom thereof so as to provide a wider base for each of the leveling legs 50 when they are placed adjacent to the underlying surface. Ultimately, the leveling legs 50 can expand downwardly for such a distance, if necessary, so as to lift the wheels 20 of the vehicle 12 off the ground in order to achieve a proper leveling effect for the floor 34.

Figure 4:
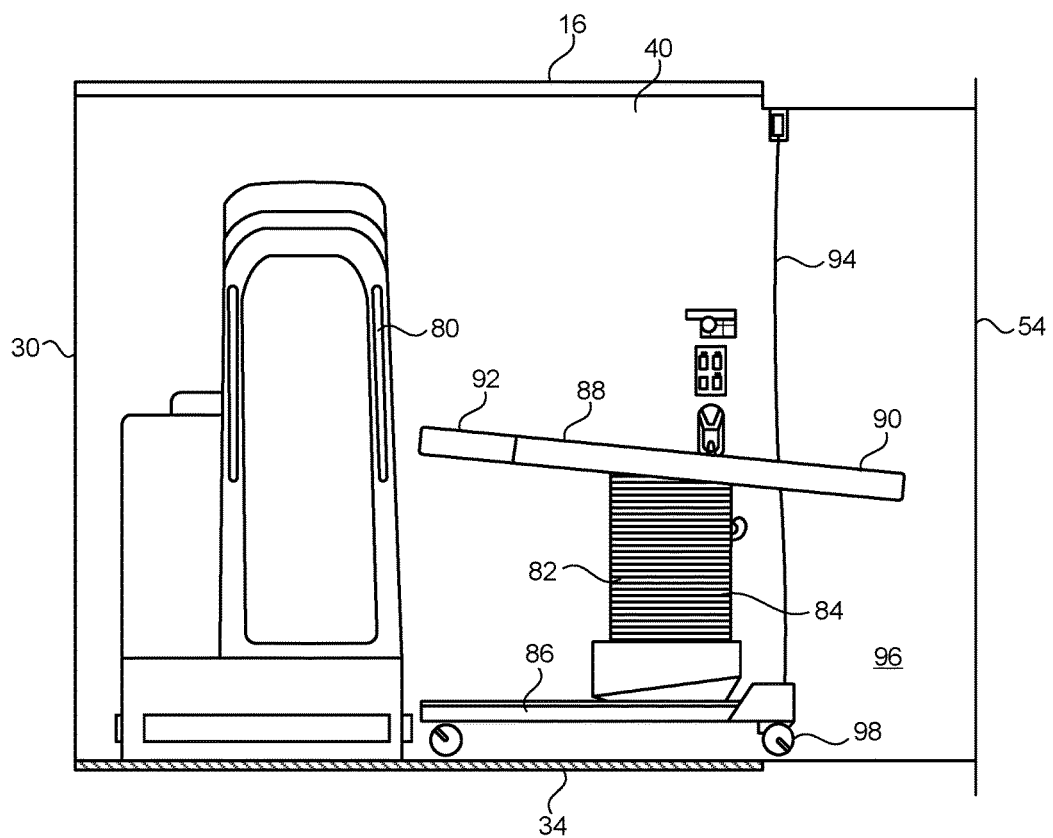
FIG. 4 is a transparent end view showing the interior of the patient compartment of the mobile screening apparatus of the present invention.

FIG. 4 shows a view of the interior 40 of the patient compartment 16. In FIG. 4, the expanding wall 54 is in its outwardly extending position. A scanner 80 is supported upon the floor 34 and extends upwardly therefrom. Scanner 80 is in generally spaced relation to the sidewall 30 of the patient compartment. The scanner 80 can be in the nature of a BODYTOM (™) or a CERETOM (™) scanner. A scanning table 82 is also supported above the floor 34 of the patient compartment 16. The scanning table 82 includes a support structure 84 extending upwardly from a base 86. A table 88 is located on top of the support structure 84. Table 88 serves to support a patient thereon. Table 88 is illustrated as being at an inclined orientation. However, various orientations of the table 88 are possible within the concept of the present invention. The scanning table includes a portion 90 that extends outwardly into the area created by the expanded portion of the expanding wall 54. As such, the end portion 92 of the table 88 is spaced away from the scanner 80. This position of the scanning table 82 is the desired position for the patient to initially lie upon.

The base of the scanning table 82 includes wheels 98 thereon. Wheels 98 are rollably position the scanning table 92 upon the floor 34. As such, the scanning table 82 can be moved from the position shown in FIG. 4 to a position in which the end portion 92 resides within the interior of the scanner 80.

Figure 5:
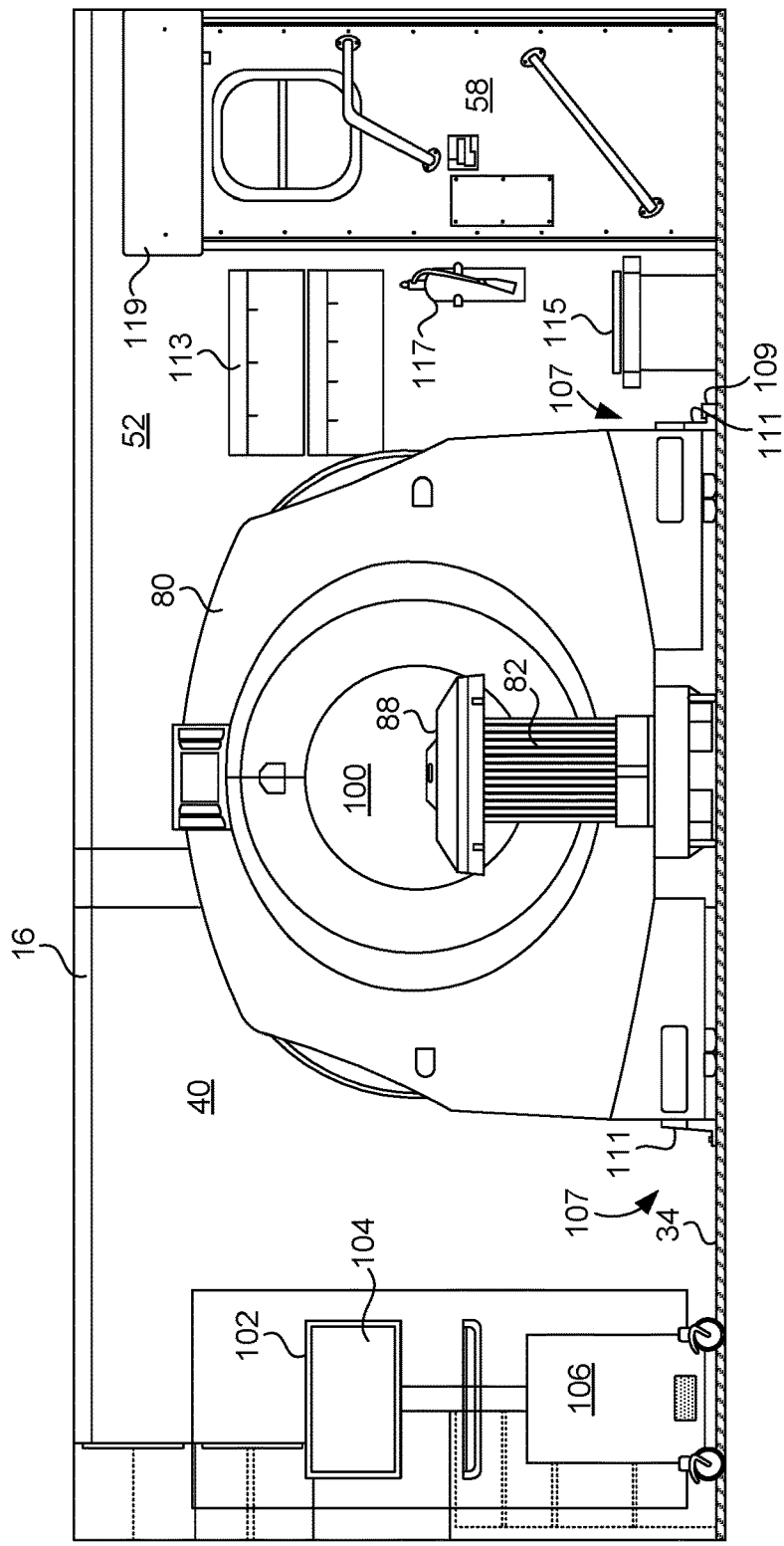
FIG. 5 is a transparent side view of the patient compartment of the mobile screening apparatus of the present invention showing, in particular, the scanner and the scanning table.

FIG. 5 shows the configuration of the scanner 80 within the interior 40 of the patient compartment 16. It can be seen that the scanner 80 includes a round or oval opening 100 at a center thereof. The table 88 of the scanning table 82 is generally aligned with this opening 100. The scanner 80 extends lengthwise within the patient compartment 16. A control system 102 is positioned at one side of the scanner 80 within the patient compartment 16. The control unit 102 can include a monitor 104 thereon so that the technician can control the operation of the scanner 80 in a conventional manner. Within the concept of the present invention, the control unit 102 can be located at either side of the scanner 80, dependent upon preferences. A rolling workstation 106 is attached to the monitor 104. Suitable ethernet portals can also be provided for use with the scanner 80.

In FIG. 5, it can be seen that the scanner 80 extends upwardly from the floor 34 of the patient compartment 16. The scanner 80 has a length dimension that is greater than a width dimension. The length dimension of the scanner 80 extends longitudinally in the interior 40 of the patient compartment 16. As such, the circular or oval opening 100 will face the expanding wall of the patient compartment 16.

The scanner 80 can be moved from a position adjacent to the fixed side wall 52 to a position centrally of the patient compartment 16. As such, the scanner 80 includes a slide mechanism 107 at the bottom thereof. The slide mechanism 107 includes a track plate 109 and a slide plate 111. This particular construction is illustrated in greater detail in FIGS. 8 and 9 herein. The movement of the scanner 80 from a position adjacent to the fixed wall 52 to a position central of the patient compartment 16 will enhance the maneuverability of the vehicle 12. In other words, this will centralize the center-of-gravity of the vehicle. If the scanner 80 were maintained at one side of the patient compartment 16, then this could cause an imbalance in the vehicle 12 and impair the maneuverability of the vehicle. As such, when the scanner 80 is intended to be used, it can be moved, by way of the slide mechanism 107, from the central position to the position generally adjacent to the fixed wall 52. A locking pin can be used so as to engage suitable holes between the slide plate 111 and the track plate 109. As such, the scanner 80 is locked into position.

FIG. 5 also shows various other items that can be located within the patient compartment 16. In particular, brochure holders can be affixed to the sidwall 52. A trash receptacle 115 can be a placed upon the floor 34. A fire extinguisher 117 can also be mounted to the sidewall 52. The first door 58 is illustrated as positioned at one end of the patient compartment. A head knocker 119 is located above the first door 58 so as to provide a cushioning effect if a person's head should encounter the sidewall 52 of the patient compartment 16.

In FIG. 5, it can be seen that the scanner has a considerable length (approximately 100 inches). As such, the length of the scanner 80 would be too great to extend widthwise within the patient compartment 16. As such, the only feasible position for the scanner 80 is generally adjacent to one of the sidewalls of the patient compartment 16. In this case, the scanner 80 resides adjacent sidewall 52. One approach would be to expand the width of the patient compartment so as to accommodate the scanner 80. However, if the width of the patient compartment were expanded so as to be in excess of 100 inches, it would exceed the DOT requirements for vehicles on American roads. As such, the present invention is able to achieve proper body scanning of the patients while providing the expanding wall 54 so as to increase the area between the scanner 80 and the end portion 90 of the table 88 of the scanning table 82.

Figure 6:
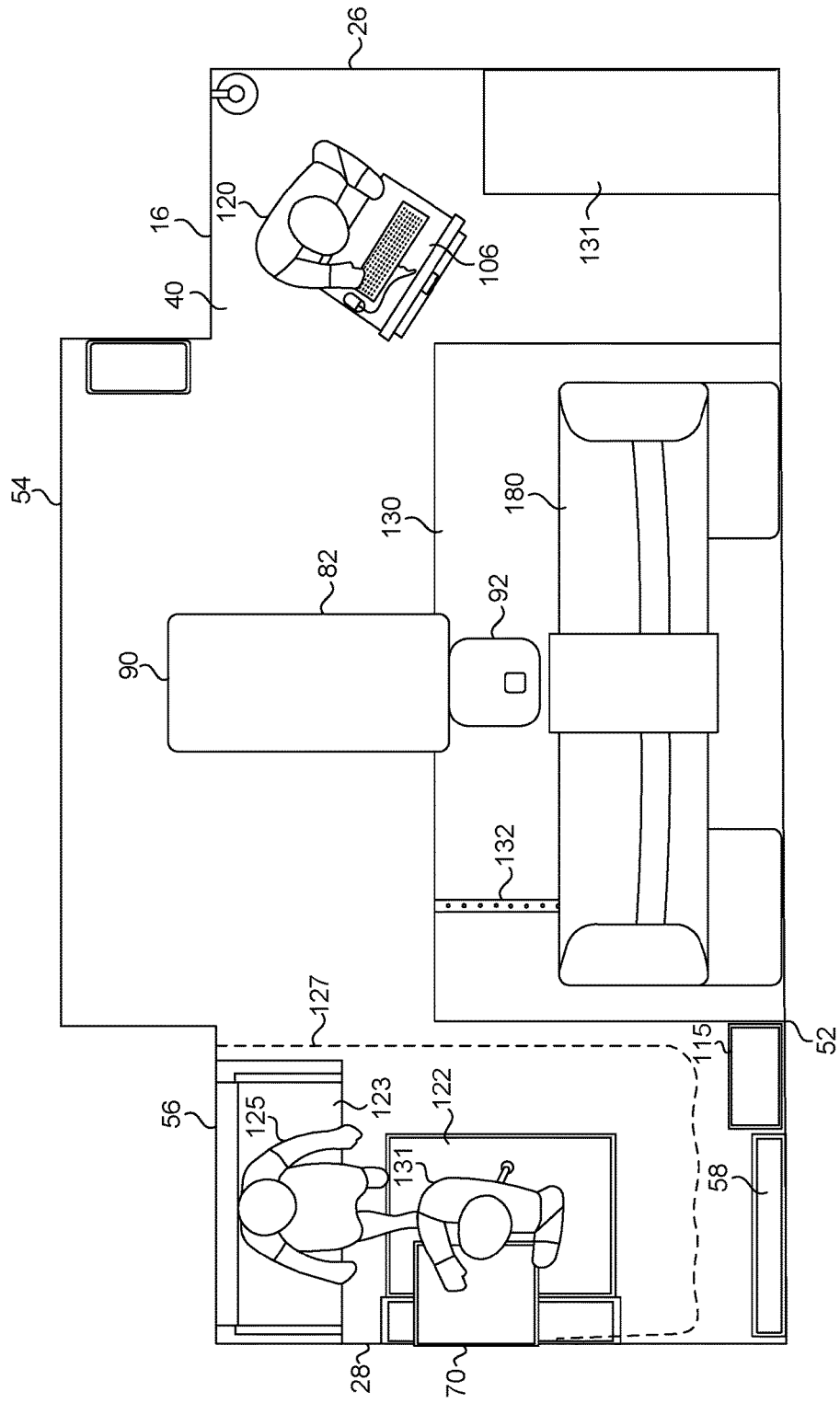
FIG. 6 is a transparent top view showing the interior of the patient compartment of the mobile screening apparatus of the present invention showing the arrangement of the scanner and the scanning table when the expanding wall is in the extended position.

FIG. 6 further shows the interior 40 of the patient compartment 16. In FIG. 6, it can be seen that the expanding wall 54 is in its extended position so as to be away from the remaining portion 56 of the sidewall. The scanning table 82 has its end portion 90 positioned within the expanded area created by the expanding wall 54. The scanning table 82 has the opposite end portion 92 positioned adjacent to the scanner 80. During use, the wheels 98 of the scanning table 82 will allow the scanning table 82 to moved to a position such that the end 92 can be located within the opening 100 of the scanner 80. Following use, the scanning table 82 can be moved to a stowage position generally adjacent to the expanding wall 54 when the expanding wall is in its retracted position. Since the patient compartment 16 will not have personnel therein during the movement of the vehicle 12, the scanning table 82 can be configured so as to extend lengthwise within the patient compartment 16. As will be described hereinafter, it can be generally locked to the floor 34 or against the inner surface of the expanding wall 54 when the expanding wall 54 is in the retracted position.

FIG. 6 shows that a technician 120 is seated at the rolling workstation 106 associated with the control unit 102. There is a wheelchair lift pressure mat 122 generally adjacent to the door 70 located at the rear wall 28 of the vehicle 12. A bench seating area 123 can extend outwardly of the sidewall 58 generally adjacent to the rear wall 28. As such, a person 125 can be seated on the bench seat 123. A privacy curtain 127 can extend in an area adjacent to the rear wall 28 of the patient compartment 16. In particular, the privacy curtain 128 is illustrated as extending from the sidewall 56 in a generally rectangular pattern and over to the rear wall 28. As such, the patient 125 can dress or undress in privacy within the interior 40 of the patient compartment 16. A flip-up table 129 can be positioned at the interior surface of the second door 70 so that the technician 131 can fill out questionnaires or other forms associated with the patient 125. The use of the privacy curtain 127 provides a certain amount of comfort and privacy to the patient 125 during the questioning of the patient by the technician 131.

The entry door 58 is illustrated at the sidewall 52 of the patient compartment 16. The trash can 115 is also illustrated as located adjacent to the first door 58. A countertop 131 is illustrated adjacent to the front wall 26 of the patient compartment 16.

The scanner 80 is positioned upon floor plate 130. Floor 130 supports the scanner 80 and allows the scanner to move from the position shown in FIG. 6 to a position generally adjacent to the center of the patient compartment 16 by way of its centipedes. As stated hereinbefore, while the vehicle is traveling, is important that the very heavy scanner 80 be moved to a position which centralizes the center-of-gravity of the patient compartment 16. Tracks 132 allow for the proper movement of the scanner 82 to the center position.

Figure 7:
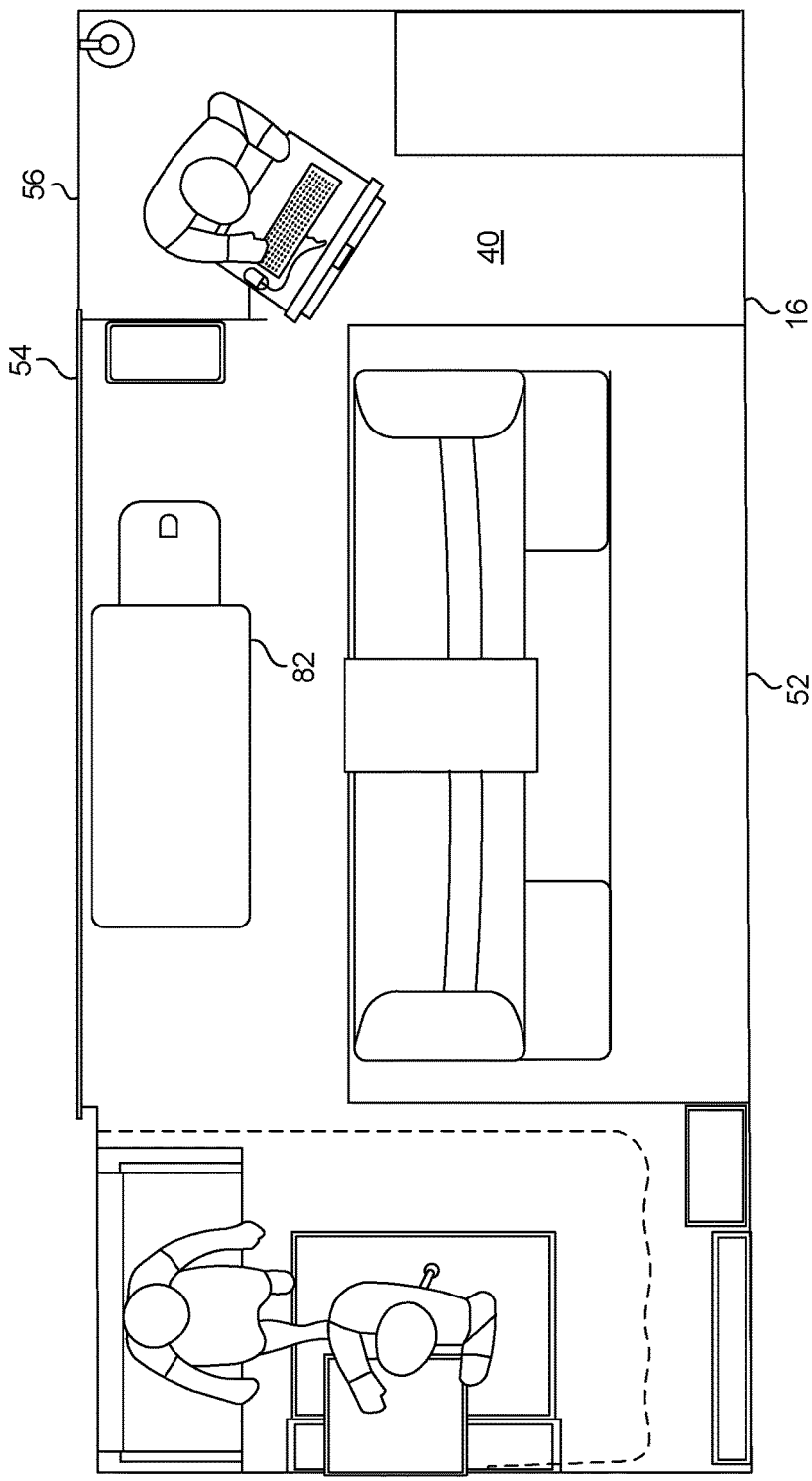
FIG. 7 is a transparent top view of the interior of the patient compartment of the mobile screening apparatus the present invention showing the arrangement of the scanner and the scanning table when the expanding wall is in the retracted position.

FIG. 7 shows that the expanding wall 54 has been retracted so as to be generally flush with the remaining sidewall 56. In this configuration, the scanning table 82 is moved from its location transverse to the expanding wall 54 in FIG. 6 to a position extending generally parallel to the expanding wall 54. In this position, the scanning table 82 can be locked against the inner wall and floor of the expanding wall 54. Similarly, the scanner 80 has been moved to a location central of the patient compartment 16 and away from the fixed wall 52. In this position, the vehicle 12 will now be suitable for travel on roadways and other surfaces. During this movement, the various personnel that are illustrated as located within the interior 40 of the patient compartment would, of course, be seated within the cabin 14 of the vehicle 12.

Figure 8:
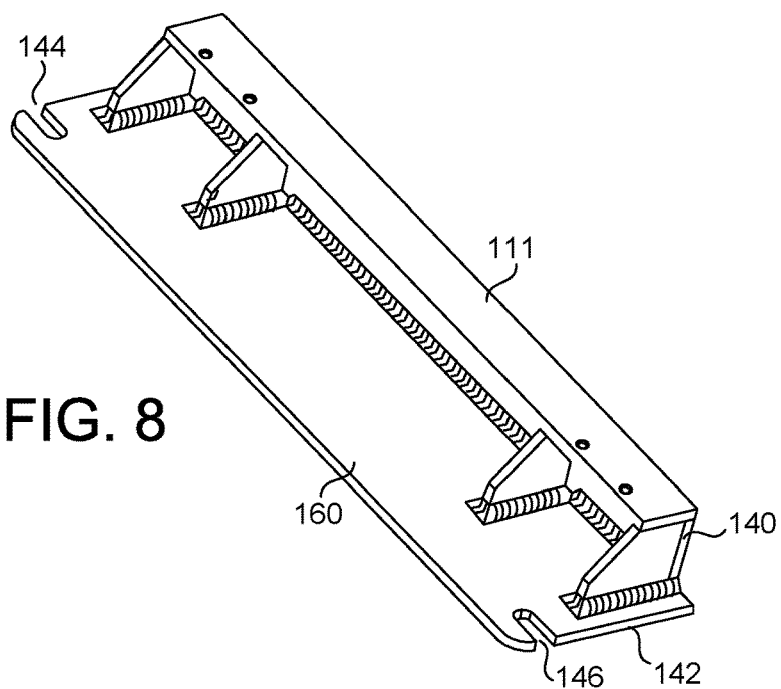
FIG. 8 is a perspective view showing the slide plate as used on the scanner of the mobile screening apparatus of the present invention.

FIG. 8 shows the slide plate 111, is illustrated previously in FIG. 5. As can be seen, the slide plate 111 includes a bracket 140 that is adapted to be fixed to the frame of the scanner 80. As such, the planar slide surface 142 will extend outwardly in generally parallel spaced relation to the floor 34 of the patient compartment 16. The planar slide surface 142 has notches 144 and 146 at opposite ends thereof. These notches 144 and 146 serve to secure the slide plate 111 to the track plate 109.

Figure 9:
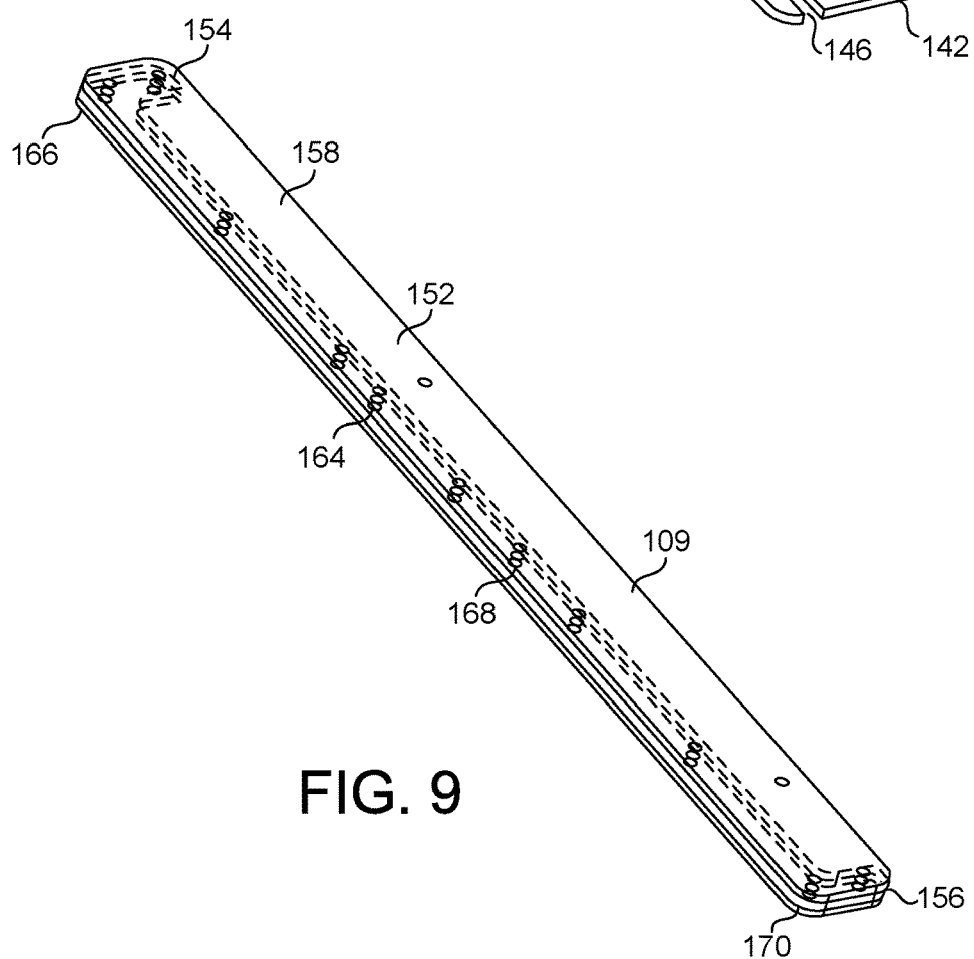
FIG. 9 is a perspective view of the tracking plate as used in cooperation with the slide plate of the mobile screening apparatus of the present invention.

FIG. 9 shows the track plate 109. In particular, there is an inset area 152 formed between inwardly turned ends 154 and 156 of the track plate 109. In general, the track plate 109 will be of a somewhat laminated construction. As such, there will be a top planar surface 158 which overlies the inset area 152.

The outwardly extending portion 160 of the slide plate 111 will be received within the inset area 152 of the track plate 109. As the scanner 80 moves from one position to the other, the outwardly extending portion 160 will move from one end 154 of the track plate 109 to the opposite end 156 of the track plate 109. When it is at the end 154, lock pins can be inserted into respective holes 164 and 166 of the track plate 109. When the outwardly extending surface 160 of the slide plate 111 moves to the end 156, pins can be inserted into respective holes 168 and 170 and through the respective notches 144 and 146 so as to lock the scanner 80 into the desired position. Suitable push-type pins can be utilized so as to securely fix the notches 144 and 146 with the respective holes in the track plate 109.

The present invention provides a mobile screening apparatus which allows the body scanning device is to be transported to remote locations. Since the mobile screening apparatus of the present invention includes an eight kilowatt generator, sufficient power is provided by the generator of the vehicle so as to meet the proper operating requirements of the scanner 80. As such, external power supplies are not required. If the external power supplies are available, then they can be connected to the shore power connection 42. The mobile screening clinic 10 of the present invention can be moved to a convenient location so as to properly screen patients without the need for patients to travel extreme distances and encounter significant difficulties in order to obtain a proper lung screening. Additionally, in the event of a chemical exposure which affects many people, the mobile screening apparatus of the present invention can move to this area of disturbance in order to carry out an immediate evaluation of the people exposed to potentially lung-damaging chemicals. In all circumstances, the mobile screening apparatus 10 of the present invention can be in complete compliance with DOT requirements when the expanding wall is in the retracted position. It is only when the mobile screening apparatus 10 reaches its intended destination that the expanding wall will be in its expanded condition. The present invention provides the ability to achieve a relatively immediate analysis and diagnosis for those in a remote location.

The foregoing disclosure and description of the invention is illustrative an explanatory thereof. Various changes in the details the illustrated construction can be made within the scope the appended claims without the parting from the true spirit of the invention. The present invention should only be limited by the following claims and their legal equivalents.

I claim:

1. A mobile screening apparatus comprising:
   a patient compartment having a floor, an end wall, a first sidewall and a second sidewall, said second sidewall having an expanding wall that is slidable between a retracted position and an extended position;
   a vehicle having a chassis upon which said patient compartment is positioned, said vehicle having wheels rotatably mounted to said chassis so as to allow said vehicle to move along an underlying surface;
   a scanner positioned in said patient compartment, said scanner having a length dimension and a width dimension, said length dimension extending longitudinally within said patient compartment such that said length dimension of said scanner is aligned with a longitudinal axis of said patient compartment, said length dimension being greater than said width dimension, said scanner having a circular or oval opening.

2. The mobile screening apparatus of claim 1, further comprising:
   a scanning table positioned in said patient compartment, said scanning table being movable in relation to said scanner, said scanning table having a surface thereon adapted to allow to allow a body to be positioned thereon.

3. The mobile screening apparatus of claim 1, further comprising:
   a generator connected to said scanner so as to supply power to said scanner.

4. The mobile screening apparatus of claim 1, said vehicle having a cabin positioned forwardly of said patient compartment.

5. The mobile screening apparatus of claim 1, further comprising:
a leveling mechanism connected or interconnected to said patient compartment, said leveling mechanism adapted to adjust said floor to a horizontal orientation relative to an underlying surface.

6. The mobile screening apparatus of claim 5, said leveling mechanism comprising:
a first leveling leg; and
a second leveling leg extending downwardly, said first leveling leg being in spaced relation to said second leveling leg.

7. The mobile screening apparatus of claim 1, said retracted position of said expanding wall being generally flush with said second sidewall.

8. The mobile screening apparatus claim 1, said first sidewall being a fixed wall.

9. A mobile screening apparatus comprising:
a patient compartment having a floor, an end wall, a first sidewall and a second sidewall, said second sidewall having an expanding wall that is slidable outwardly from said second sidewall from a retracted position to an extended position;
a scanner positioned in said patient compartment, said scanner having a length dimension and a width dimension, said length dimension being greater than said width dimension, said scanner having a circular or oval opening, said scanner being movable within said patient compartment between a first position in which said length dimension is parallel to and adjacent said first sidewall and a second position generally centrally of said patient compartment in which said length dimension is parallel to said first sidewall.

10. The mobile screening apparatus of claim 9, said scanner being at said first position when said expanding wall is in said extended position, said scanner being in said second position when said expanding wall is in said retracted position.

11. The mobile screening apparatus of claim 9, further comprising:
a track plate affixed to said floor of said patient compartment; and
a slide plate received by said track plate, said slide plate movable from one end to an opposite end of said track plate as said scanner moves between the first and second positions.

12. The mobile screening apparatus of claim 11, further comprising:
a locking pin received by said track plate and said slide plate so as to fix the position of said scanner in said patient compartment.

13. The mobile screening apparatus of claim 2, said scanning table movable between a stowed position and an active position, said stowed position being against that expanding wall when said expanding wall is in the retracted position, said scanning table extending transverse to said expanding wall when said expanding wall is in the extended position.

14. The mobile screening apparatus of claim 1, said scanner being a lung scanner.

15. The mobile screening apparatus of claim 1, further comprising:
a control system positioned in said patient compartment and cooperative with said scanner.

16. The mobile screening apparatus of claim 1, said floor of said patient compartment having an area when said expanding wall is in said extended position that is greater than an area when said expanding wall is in said retracted position.

17. The mobile screening apparatus of claim 1, said patient compartment having a first door at one of said first and second sidewalls, said patient compartment having a second door at said end wall.

18. A mobile screening apparatus comprising:
a patient compartment having a floor, and end wall, a first sidewall and a second sidewall, said second sidewall having an expanding wall that is slidable between a retracted position and an extended position;
a scanner positioned in said patient compartment, said scanner having a length dimension and a width dimension, said length dimension extending longitudinally within said patient compartment such that said length dimension of said scanner is aligned with a longitudinal axis of said patient compartment, said length dimension being greater than said width dimension, said scanner having a circular or oval opening;
a vehicle having a chassis upon which said patient compartment is positioned, said vehicle having wheels rotatably mounted to said chassis so as to allow said vehicle to move along an underlying surface, said vehicle having a cabin positioned forwardly of said patient compartment;
a scanning table positioned in said patient compartment, said scanning table being movable in relation to said scanner, said scanning table having a surface thereon adapted to allow a body to be positioned thereon, said scanning table movable between a stowed position and an active position, said scanning table being against said expanding wall in the stowed position, said scanning table extending transverse to said expanding wall when said expanding wall is in the extended position; and
a generator connected to said scanner so as to supply power to said scanner, said generator being mounted to said patient compartment or to said vehicle.

* * * * *